United States Patent
Ismailer et al.

(10) Patent No.: US 6,352,687 B1
(45) Date of Patent: *Mar. 5, 2002

(54) NAIL ENAMEL COMPOSITION CONTAINING LIGHT REFLECTING MATERIAL

(75) Inventors: Anatoly Ismailer, Roslyn Heights, NY (US); Robert L. Socci, Cedar Grove, NJ (US)

(73) Assignee: Kirker Enterprises, Inc., Paterson, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/361,050

(22) Filed: Jul. 26, 1999

(51) Int. Cl.$^7$ .................................. A61K 7/04
(52) U.S. Cl. .................. 424/61; 424/400; 424/401; 424/59; 424/61
(58) Field of Search .......... 424/61, 70.1, 401; 524/40

(56) References Cited

U.S. PATENT DOCUMENTS

| | | |
|---|---|---|
| 3,301,760 A | 1/1967 | Jewel |
| 3,954,693 A | 5/1976 | Fong |
| 4,174,386 A | 11/1979 | Spitzer et al. |
| 4,439,494 A | 3/1984 | Olson .................. 428/412 |
| 4,482,538 A | 11/1984 | Davies |
| 4,626,428 A | 12/1986 | Weisberg et al. |
| 4,665,116 A | 5/1987 | Kornhaber et al. |
| 4,669,491 A | 6/1987 | Weisberg et al. |
| 4,832,944 A * | 5/1989 | Socci et al. .................. 424/61 |
| 4,943,462 A | 7/1990 | Komerska et al. |
| 4,954,619 A | 9/1990 | Lang et al. |
| 5,071,639 A | 12/1991 | Soyama et al. ............... 424/61 |
| 5,133,966 A * | 7/1992 | Khamis .................. 424/401 |
| 5,276,075 A * | 1/1994 | Santini ................... 524/40 |
| 5,306,739 A | 4/1994 | Lucey |
| 5,330,750 A | 7/1994 | Sheard et al. |
| 5,407,666 A | 4/1995 | Patel et al. |
| 5,516,509 A | 5/1996 | Marr-Leisy et al. |
| 5,538,717 A | 7/1996 | LaPoterie .................... 424/61 |
| 5,543,085 A | 8/1996 | Miner |
| 5,612,397 A | 3/1997 | Gebhard et al. |
| 5,639,447 A * | 6/1997 | Patel .......................... 424/61 |
| 5,650,159 A | 7/1997 | Lion et al. .................. 424/401 |
| 5,725,866 A | 3/1998 | Ramin |
| 5,833,967 A * | 11/1998 | Ramin ....................... 424/70.4 |

FOREIGN PATENT DOCUMENTS

| | | |
|---|---|---|
| EP | 0300234 | 6/1988 |
| EP | 0453628 A2 | 10/1990 |
| EP | 0504754 A1 | 3/1991 |
| FR | 1453089 | 5/1965 |
| JP | 60016910 | 1/1985 |

OTHER PUBLICATIONS

Merriam–Webster's Collegiate Dictionary, Tenth Edition, 1998, p. 1255.*
L'Ongle: Griffe Ou Ornement by H. Djelassi, J.J. Berjon, D. Saboureau, D. Heran.
Tevco Ingredient List.
Cabot Technical Data, CAB–O–SIL® Fumed Silica in Cosmetic and Personal Care Products.
Technical Bulletin Pigments, Baasic Characteristics of AEROSIL®, Degussa AG.
CAB–O–SIL® Untreated Fumed Silica Properties and Functions, 1978, 1993 Cabot Corporation.

* cited by examiner

Primary Examiner—Thurman K. Page
Assistant Examiner—Charesse L. Evans
(74) Attorney, Agent, or Firm—Lerner, David, Littenberg, Krumholz & Mentlik, LLP

(57) ABSTRACT

A transparent nail enamel composition includes small pieces of light-reflecting decorative material in the nature of glitters, micas and/or other large-sized particles. The glitter is suspended in the nail enamel composition using fumed silica. The nail enamel composition exhibits both transparent wet and dry state clarity.

35 Claims, No Drawings

NAIL ENAMEL COMPOSITION CONTAINING LIGHT REFLECTING MATERIAL

FIELD OF THE INVENTION

The present invention relates in general to nail enamel compositions, and more particularly, to such compositions which are suitable for coating natural and synthetic nails. Still more particularly, the present invention relates to transparent nail enamel compositions which include small pieces of light-reflecting decorative material known as glitters.

BACKGROUND OF THE INVENTION

Nail enamel compositions include a class of nail care products regularly used by women as part of their beauty care routine. These nail care products are available in a multitude of product formulations, from clears to infinite colors. Typically, clear nail enamel compositions include a film forming polymer, a film forming resin, a plasticizer and one or more solvents. In the case of a color nail enamel composition, the product will also include a thixotropic compound, a suspending agent and one or more pigments, or in the alternative, an organic coloring polymer may be used. In addition to these components, a number of optional and proprietary components are often included such as UV light absorbers, moisturizers, stabilizers, fragrances and the like.

Nail enamel compositions particularly suitable as a color coat have included a variety of pigments which provide an opaque colored film. Nail enamel films having a semi-translucent color are formed using generally organic colorants which create a tint. In order to provide the nail enamel film with a more dramatic effect, there has been known the use of small pieces of light reflecting decorative materials known as glitters. Glitters are commercially available in a variety of materials, for example, polyester film with metallized coatings, aluminum foil with thermosetting coatings, polybutylene terephthalate with acrylates copolymer and acrylates copolymer polybutylene terephthalate ethylene/vinyl acetate copolymer. Other known glitters and their suppliers are disclosed in Gebhard, et al., U.S. Pat. No. 5,612,397, which glitters are incorporated herein by reference.

The desirable aesthetic properties of glitter nail enamel compositions initially depends upon their wet state clarity during the time of purchase by the consumer. Dry state clarity, on the other hand, means the clarity of the nail enamel composition in its dry state after being applied as a coating to a natural or synthetic nail. One of the problems associated with conventional glitter nail enamel compositions is the dull appearance of the glitter dispersed in the composition in their wet state. This dull appearance results from the cloudy or milky translucent or opaque appearance of the nail enamel composition resulting from the use of conventional suspending agents, in particular, modified colloidal clays such as bentonite or montmorillonite clays, for example stearalkonium hectorite.

Due to the cloudy or milky translucent or opaque appearance of conventional glitter nail enamel compositions in their wet state, it has become harder for a purchaser to appreciate the glitter of these compositions, especially when viewed from a distance, i.e., inspecting the glitter nail enamel compositions in their bottles placed on store display racks. Often, the selection of one glitter nail enamel composition over another is based upon the aesthetic appearance of the composition in its wet state. There has therefore been a need for developing glitter nail enamel compositions having improved wet state clarity.

Gebhard, et al. discloses an aqueous polymer dispersion composition for use in nail polish and artist, craft and hobby paints containing glitter having improved wet state clarity. Gebhard, et al. discloses an aqueous binder combination, i.e., an aqueous solution of a thickener having polymer particles dispersed therein, having a desirable wet state clarity index of less than 65. This is attained by matching an aqueous dispersion of polymer particles of certain size with an appropriately selected thickener. In particular, a wet state clarity index of less than 65 is attained in the binder combination when polymer particles having a diameter of less than 80 manometers are mixed with any selected thickener. In addition, when an aqueous dispersion of polymer particles having a diameter of less than 120 manometers is mixed with a polyurethane thickener in the binder combination, the desired wet state clarity index is attained. However, an aqueous dispersion of polymer particles having a diameter in excess of 120 manometers with any thickener or polymer particles having a diameter of less than 120 manometers but greater than 80 manometers with a non-polyurethane thickener produces a cloudy or milky binder composition having a wet state clarity index in excess of 65. Non-polyurethane thickeners are disclosed as including acrylic copolymer thickeners, acrylic copolymer hydrophobically modified associative thickeners, cellulose ether non-associative organic thickeners, hydrophobically modified hydroxyethyl cellulose nonassociative organic thickeners, polyethylene oxide nonassociative thickeners and polyacrylamide nonassociative thickeners.

Ramin, U.S. Pat. No. 5,725,866 discloses a pigmented nail enamel composition having translucent properties in the wet state including pyrogenic silica as a thickening agent. The composition may include inorganic or organic pigments in small quantity, as well as various particulates such as diamond particles, boron nitride particles, pearl particles and/or pumice particles. The translucent form of the nail enamel composition is defined as a non-opaque and non-opalescent form or a form allowing the passage of light without allowing the forms to be distinguished, wherein the optical density is in the range from 0.1–0.6. The translucent form of the nail enamel composition lacks the desired wet state clarity, particularly for compositions containing glitters. In this regard, the translucent form of the nail enamel composition which, although allowing some passage of light, does not allow forms within the nail enamel composition to be distinguished. It is expected that this would provide a dull appearance to the glitter dispersed in any such translucent composition when in the wet state.

There has heretofore been a desire for continuously improving the wet state clarity of nail enamel compositions, and specifically, an unsolved need for glitter containing nail enamel compositions which are transparent in their wet and dry states so as to enhance their aesthetic appearance to the consumer.

SUMMARY OF THE INVENTION

The present invention broadly discloses a transparent nail enamel composition having improved wet state clarity containing small pieces of light reflecting decorative material. The nail enamel compositions of the present invention are based upon the use of fumed silica as a suspending agent for the light reflecting material and the use of nail enamel components which produce a base having a transparent wet state, and hence, a transparent dry state.

In accordance with one embodiment of the present invention there is described a transparent nail enamel composition comprising a film forming composition containing light reflecting material and a suspending agent for the material consisting essentially of fumed silica.

In accordance with another embodiment of the present invention there is described a transparent nail enamel composition having an optical density less than 0.1 comprising a film forming polymer, a film forming resin, a solvent having a refractive index greater than about 1.40, a plasticizer, light reflecting material and a suspending agent for the material consisting essentially of fumed silica.

In accordance with another embodiment of the present invention there is described a transparent glitter nail enamel composition having an optical density less than 0.1 comprising a film forming polymer present in the range of about 5 to 40% by weight, a film forming resin present in the range of about 5 to 25% by weight, a solvent selected from the group consisting of toluene, xylene and mixtures thereof present in an amount greater than about 20% by weight, a plasticizer, glitter and a suspending agent for said glitter consisting essentially of fumed silica present in the range of about 2 to 6% by weight.

In accordance with another embodiment of the present invention there is described a method of making a nail enamel composition having a transparent wet state containing light reflecting material, the method comprising combining a film forming component, a solvent, light reflecting material and a suspending agent for the material consisting essentially of fumed silica, and selecting the solvent whereby the composition has an optical density less than 0.1.

DETAILED DESCRIPTION OF THE PREFERRED EMBODIMENTS

Nail enamel compositions of the present invention for coating natural or synthetic nails broadly include the ingredients of at least one film forming component, a solvent, light reflecting material such as glitters and a suspending agent for the light reflecting material consisting essentially of fumed silica. The resulting composition will provide a nail enamel composition having improved wet state clarity by being transparent. As used in this application, the term transparent means a base coat or nail enamel composition that transmits most of the incident light without diffusion or absorption. More specifically, it is generally intended that transparent refers to base coat or nail enamel compositions having an optical density less than 0.1, corresponding to a light transmission greater than about 80%. Below the foregoing range of optical density and light transmission, base coat or nail enamel compositions are considered to be translucent in their wet state, as opposed to being transparent in accordance with the present invention. As used in this application, glitter refers to small pieces of light reflecting decorative material. By way of example, glitters can be manufactured from any number of a variety of materials such as previously described and as disclosed in Gebhard, et al.

The glitter may be in the form of a variety of shapes, sizes and colors to provide the desired decorative effect for the resulting transparent glitter nail enamel composition. For example, the glitter may be in the form of flat flakes having any desirable shape, such as irregular, square, round, oval, star, triangular and the like. The glitter may also have a more three dimensional form, for example, such as spheres, cubes, rods and the like. In addition, the glitter may be of any desirable color or combinations of colors, as well as any irregular, random or predetermined pattern of colors. The amount of glitter which can be incorporated in the nail enamel compositions of the present invention can widely vary depending upon the decorative effect desired. By way of example only, the amount of glitter may range from about 5 to 20% by weight of the nail enamel composition.

In addition to, or in the alternative, the nail enamel compositions of the present invention may include other large light reflecting particles such as micas and aluminum particles. Preferably, the particles will have a particle size range greater than about 50 microns. Accordingly, the present invention is not limited to the light reflecting particles being only glitter.

The nail enamel compositions contain one or more film forming components such as film forming polymers, for example, cellulose acetate, cellulose acetate butyrate, ethyl cellulose, vinyl polymers, nitrocellulose, as well as methacrylate and acrylate type polymers, and mixtures thereof. Nitrocellulose provides an unusual combination of properties of toughness, durability, solubility and solvent release. Examples of nitrocellulose are the so called nitrocellulose RS $1/8$ sec. and $1/4$ sec.; nitrocellulose $1/2$ sec.; and nitrocellulose RS 5–6 sec. and 60–80 sec., which have higher viscosities than the earlier grades. The term "RS" refers to the brand of nitrocellulose with a nitrogen content of about 11.2–12.8% with solubility in esters, ketones and glycol ethers manufactured by Hercules, Inc. The terms $1/8$ sec., $1/4$ sec., $1/2$ sec., 5–6 sec., etc. represent viscosity and refer to the time it takes for a ball to fall to a given depth in the material. Nitrocellulose is typically supplied in 70% concentrations, wet with 30% ethyl or isopropyl alcohol. As used in the present application, the percentage of nitrocellulose in a given composition will be on a wet basis. Nail enamel compositions of the present invention may include film forming polymers and combinations thereof in an amount ranging from about 5 to 40% by weight, and more preferably in the range of about 10 to 20% by weight.

In addition to the aforementioned film forming polymers, the nail enamel compositions can also include one or more film forming resins. Exemplary film forming resins which may be used in the present invention either alone or in combination with the film forming polymers include, for example, drying and non-drying alkyd resins, polyvinyl resins for example polyvinyl acetate, polyester resins, epoxy resins, acrylic polymers and copolymers, maleic modified glycerol esters of rosin, and toluene sulfonamide/epoxy resins, e.g., tosylamide epoxy resin. It is also within the scope of nail enamel compositions of the present invention to include aldehyde condensation products such as arylsulfonamide formaldehyde resins, specifically toluene sulfonamide formaldehyde resin which is a condensation product of formaldehyde and toluene sulfonamide. The amount of film forming resin and combinations thereof can range from about 5 to 25% by weight of the composition, and preferably about 5 to 10% by weight of the composition.

In addition to the film forming components, the nail enamel compositions according to the present invention will generally include at least one plasticizer to soften and plasticize particularly the film forming polymer. The plasticizer may be in either liquid or solid form, as well as combinations thereof. The nail enamel compositions may include one or more of the known plasticizers which are suitable for use in nail enamel compositions. Examples of such known plasticizers include tricresyl phosphate, dibutyl tartrate, benzyl benzoate, tributyl phosphate, butyl acetyl ricinoleate, butyl glycolate, butyl stearate, triphenyl phosphate, triethyl citrate, camphor, castor oil, esters of citric, stearate, phalic, oleic, phosphate, butyric and benzoic acid, glyceryl triacetate and glyceryl triproprionate, 2, 2, 4-trimethyl-1, 3-pentandiiol diisobutyrate and mixtures thereof. The nail enamel compositions of the present invention also contemplate the use of phthalate type plasticizers either alone or in combination with the aforementioned plasticizers, for example, diamylphthalate, dibutyl phthalate, diethyl phthalate, dioctyl phthalate, dibutoxy ethylphthalate and mixtures thereof.

Plasticizers included in the compositions of the present invention are in amounts sufficient to provide acceptable flexibility to the nail enamel film on the human or synthetic nail surface. In this regard, the amount of plasticizer and combinations thereof for use in the nail enamel compositions of the present invention range from about 2 to 15% by weight, and preferably about 5 to 10% by weight.

The nail enamel compositions of the present invention also include one or more solvents such as those generally used in conventional nail enamel compositions. Examples of these solvents include ethyl acetate, methyl acetate, ethanol, isopropanol, propyl acetate, n-butanol, aromatic (containing phenyl groups), amyl acetate, ethers, toluene, ketones, alkanes for example, pentane, cyclopentane, hexane, heptane, cyclohexane, cyclic ethers for example, tetrahydrofuran and 1,4-dioxane, cellosolve, butyl cellosolve acetate, cellosolve acetate, methyl cellosolve acetate, butyl cellosolve, ethyl cellosolve, phenylated solvents for example, xylene, esters of acetic acid for example, methyl acetate, ethyl acetate, n-butyl acetate, chlorinated hydrocarbons for example, methylene chloride, chloroform and methylchloroform. The aforementioned solvents can be used alone or in mixtures thereof. In general, the amount of solvent used in the compositions of the present invention range from about 50 to 80% by weight, and preferably about 65 to 75% by weight.

As previously described, the use of conventional suspending agents such as bentonite has resulted in known glitter nail enamel compositions having poor wet state clarity by having a translucent, cloudy or milky appearance. It has been discovered that by using fumed silica as a suspending agent in nail enamel compositions of the present invention, a glitter nail enamel composition having a transparent wet state clarity can be obtained. Fumed silica is available from a number of companies, for example, Degussa of Germany sold under the trademark Aerosil and Cabot Corporation of Tuscola, Ill. sold under the trademark Cab-O-Sil. Various grades of fumed silica are available from either of the aforementioned companies which can be used as a suspending agent in accordance with the present invention. By way of one example, the particular fumed silica used in the examples to be described was Aerosil 200 obtained from Degussa. The amount of fumed silica used in the compositions of the present invention range from about 2 to 6% by weight, and preferably about 3 to 5% by weight.

Fumed silica was previously known for use in nail enamel compositions as a thickening agent for a pigmented composition where clarity was not required. For example, various photocurable nail enamel compositions which include fumed silica as a thickening agent are disclosed in Patel, et al., U.S. Pat. No. 5,407,666 and Marr-Leisy, et al., U.S. Pat. No. 5,516,509. In addition, there is disclosed in Sheard, et al., U.S. Pat. No. 5,330,750 the addition of fumed silica as an additive particularly useful in nail ridge fillers. See also the prior discussion with respect to Ramin, U.S. Pat. No. 5,725,866. It was not expected that fumed silica could be incorporated into a nail enamel composition to provide a transparent wet state, in view of the fact that it is known that fumed silica when used in a film forming composition produces a matte finish having substantially reduced glossiness in the resulting composition or a translucent wet state. To this end, it was known to use fumed silica in shellacs, lacquers, varnishes and other coatings to produce a reduced sheen which was often desirable in applications such as furniture, woodwork and other finished products.

The incorporation of fumed silica, in and of itself, in a nail enamel composition will not produce a transparent wet state composition. It has been discovered that in order to provide a transparent nail enamel composition, the overall composition should generally have a refractive index approaching the refractive index of the fumed silica, i.e., 1.46. It has been discovered that nail enamel compositions formulated with toluene as a solvent have a greater tendency to provide a transparent composition than those formulated without toluene. In this regard, toluene has a refractive index of 1.497 which is higher than that of fumed silica. By way of theory only, it is believed that the presence of toluene will increase the refractive index of the nail enamel composition to more closely approach 1.46 where the other components have a lower refractive index, e.g., ethyl acetate—1.372, butyl acetate—1.394, etc. In addition to toluene, other solvents such as xylene having a refractive index ranging from 1.40 to 1.50 are contemplated as suitable for use in accordance with the present invention which will provide a nail enamel composition having a transparent wet state when incorporating fumed silica.

It is contemplated that a transparent nail enamel composition of the present invention can be formulated using conventional non-toxic components such as those components identified herein, and by including toluene or a toluene substitute as noted hereinabove. It is further contemplated that toluene or its equivalent should be present in the nail enamel formulation in an amount greater than about 20%, and preferably in an amount greater than about 25%. The use of toluene or a toluene substitute enables the use of traditional nail enamel components to provide a nail enamel composition having a transparent wet state suitable for incorporation of various glitters.

One or more known organic colorants may also be added to these compositions to provide a color tint to the resulting film. Suitable organic colorants are well known in the nail enamel art. In addition, a small quantity of one or more pigments can be added to the glitter nail enamel composition to provide a different color effect to the resulting glitter films. Pigments for use in the present invention may include any of those pigments which are generally known for use in nail enamel compositions. In addition, there may also be included titanated micas, polyethylene terephthalates and pearl essence which is a suspension of crystalline guanine in nitrocellulose and solvents. Although pigments can be used in the nail enamel composition of the present invention, the presence of pigments will affect the wet state clarity. However, various decorative effects can be achieved by the combination of the use of glitters and pigments if desired.

In addition to the above described components, the compositions of the present invention may also include additional additives including stabilizers, UV light absorbers, fragrances, moisturizers and medicants, depending on the intended result. These components are well known in the art and may be included in amounts well within the teachings of the prior art.

The nail enamel compositions in accordance with the present invention can be manufactured by thoroughly and intimately mixing together all the components in the amounts described in accordance with the present invention.

Examples of satisfactory equipment and how to use then are readily apparent to one of ordinary skill in the nail enamel art.

The following examples are provided to illustrate the transparent nail enamel compositions of the present invention and should not be construed to limit the scope of the invention in any way.

EXAMPLE 1

|  | WT. % |
|---|---|
| toluene | 26.60 |
| nitrocellulose ¼ sec. | 15.2 (wet) |
| polyester resin | 8.9 |
| dibutyl phthalate | 6.25 |
| butyl acetate | 20.47 |
| isopropyl alcohol | 8.08 |
| Aerosil 200 (fumed silica) | 3.50 |
| glitter | 11.00 |
|  | 100.00 |

|  | WT. % |
|---|---|
| toluene | 32.00 |
| acrylates copolymer | 7.00 |
| cellulose acetate butyrate | 10.00 |
| toluenesulfonamide epoxy resin | 8.00 |
| isopropyl alcohol | 10.00 |
| butyl acetate | 18.00 |
| dibutyl phthalate | 4.00 |
| Aerosil 200 (fumed silica) | 3.00 |
| glitter | 8.00 |
|  | 100.00 |

|  | WT. % |
|---|---|
| xylene | 26.80 |
| nitrocellulose ½ sec. | 15.0 (WET) |
| tosylamide formaldehyde resin | 9.15 |
| dibutyl phthalate | 6.00 |
| butyl acetate | 20.60 |
| isopropyl alcohol | 8.55 |
| aerosil 200 (fumed silica) | 4.00 |
| glitter | 10.00 |
|  | 100.00 |

The above examples provide a glitter nail enamel composition having a transparent wet state unlike known nail enamel compositions which include, for example, known suspending agents such as bentonite in a glitter nail enamel composition.

Although the invention herein has been described with reference to particular embodiments, it is to be understood that the embodiments are merely illustrative of the principles and application of the present invention. For example, minor amounts of conventional suspending agents such as colloidal clays and montmorillonite may be added to the fumed silica with only a contemplated small decrease in wet state clarity, e.g., optical density or light transmission. Thus, the use of minor amounts of conventional suspending agents in combination with fumed silica is considered within the scope of the present invention where a transparent composition results. Therefore to be understood that numerous modifications may be made to the embodiments and that other arrangements may be devised without departing from the spirit and scope of the present invention as defined by the claims.

What is claimed is:

1. A transparent wet state nail enamel composition comprising a film forming composition containing light reflecting material, a plurality of solvents and a suspending agent for said material consisting essentially of fumed silica, said plurality of solvents and their respective amounts being selected wherein said composition in the absence of said light reflecting material is transparent and has an optical density less than 0.1.

2. The composition of claim 1, wherein said film forming composition includes a film forming component and a plasticizer.

3. The composition of claim 2, wherein said film forming component is selected from the group consisting of nitrocellulose, polyester resin, cellulose acetate butyrate, epoxy resin, toluene sulfonamide formaldehyde resin, tosylamide formaldehyde resin, acrylates copolymer and mixtures thereof.

4. The composition of claim 2, wherein said film forming component is present in the range of about 5 to 40% by weight and said solvents are present in the range of about 50 to 80% by weight.

5. The composition of claim 2, wherein said light reflecting material is present in the range of about 0.5 to 20% by weight.

6. The composition of claim 2, wherein at least one of said solvents has a refractive index greater than 1.40.

7. The composition of claim 6, wherein at least one of said solvents is selected from the group consisting of toluene, xylene and mixtures thereof.

8. The composition of claim 2, wherein said solvent is toluene present in an amount greater than about 20% by weight.

9. The composition of claim 1, wherein said fumed silica is present in the range of about 2 to 6% by weight.

10. The composition of claim 1, wherein said light reflecting material comprises glitter.

11. The composition of claim 1, wherein said film forming composition includes a film forming polymer, a film forming resin and a plasticizer.

12. The composition of claim 11, wherein at least one of said solvents comprises toluene.

13. The composition of claim 12, wherein said fumed silica is present in the range of about 2 to 6% by weight.

14. A transparent wet state nail enamel composition comprising a film forming polymer, a film forming resin, a plurality of solvents, at least one of said solvents having a refractive index greater than about 1.40, a plasticizer, light reflecting material and a suspending agent for said material consisting essentially of fumed silica, said plurality of solvents and their respective amounts being selected wherein said composition in the absence of said light reflecting material is transparent and has an optical density less than 0.1.

15. The composition of claim 14, wherein said film forming polymer and said film forming resin are selected from the group consisting of nitrocellulose, polyester resin, cellulose acetate butyrate, epoxy resin, toluene sulfonamide formaldehyde resin, tosylamide formaldehyde resin, acrylates copolymer and mixtures thereof.

16. The composition of claim 14, wherein said film forming polymer is present in the range of about 5 to 25% by weight and said film forming resin is present in the range of about 5 to 15% by weight.

17. The composition of claim 14, wherein said fumed silica is present in the range of about 2 to 6% by weight.

18. The composition of claim 14, wherein said light reflecting material comprises glitter.

19. The composition of claim 14, wherein at least one of said solvents is selected from the group consisting of toluene, xylene and mixtures thereof.

20. The composition of claim 14, wherein at least one of said solvents comprises toluene present in an amount greater than about 20% by weight.

21. A transparent wet state glitter nail enamel composition comprising a film forming polymer present in the range of about 5 to 40% by weight, a film forming resin present in the range of about 5 to 25% by weight, a primary solvent selected from the group consisting of toluene, xylene and mixtures thereof present in an amount greater than about 20% by weight, at least one secondary solvent, a plasticizer, glitter and a suspending agent for said glitter consisting essentially of fumed silica present in the range of about 2 to 6% by weight, said solvents and their respective amounts selected wherein said composition in the absence of said glitter is transparent and has an optical density less than 0.1.

22. The composition of claim 21, wherein said glitter comprises small pieces of light-reflecting decorative material.

23. The composition of claim 21, further including an inorganic colorant.

24. A method of making a nail enamel composition having a transparent wet state containing light reflecting material, said method comprising combining a film forming component, a plurality of solvents, light reflecting material and a suspending agent for said material consisting essentially of fumed silica, and selecting said solvents and the amounts thereof whereby said composition in the absence of said light reflecting material is transparent and has an optical density less than 0.1.

25. The method of claim 24, wherein at least one of said solvents is selected from the group consisting of toluene, xylene and mixtures thereof.

26. The method of claim 24, wherein at least one of said solvents has a refractive index greater than about 1.40.

27. The method of claim 24, wherein said solvents are present in an amount of about 50 to 80% by weight.

28. The method of claim 24, wherein said fumed silica is present in an amount of about 2 to 6% by weight.

29. The method of claim 24, wherein said light reflecting material comprises glitter.

30. The method of claim 24, wherein said film forming component is selected from the group consisting of nitrocellulose, polyester resin, cellulose acetate butyrate, epoxy resin, toluene sulfonamide formaldehyde resin, tosylamide formaldehyde resin, acrylates copolymer and mixtures thereof.

31. A transparent glitter containing nail enamel composition made in accordance with the method of claim 24.

32. A method of making a nail enamel composition having a transparent wet state containing light reflecting material, said method comprising combining a film forming component, a plurality of solvents, light reflecting material, a plasticizer for said film forming component and a suspending agent for said material consisting essentially of fumed silica, and selecting said solvents and the respective amounts thereof such that said composition in a wet state has a refractive index of about 1.46 and an optical density less than 0.1 in the absence of said light reflecting material and wherein said composition is transparent.

33. The method of claim 32, wherein at least one of said solvents comprises toluene.

34. The method of claim 32, wherein at least one of said solvents comprises xylene.

35. A transparent nail enamel composition containing glitter as said light reflecting material made in accordance with claim 32.

* * * * *

UNITED STATES PATENT AND TRADEMARK OFFICE
CERTIFICATE OF CORRECTION

PATENT NO.   : 6,352,687 B1
DATED        : March 5, 2002
INVENTOR(S)  : Anatoly Ismailer and Robert L. Socci It is certified that error appears in the above-identified patent and that said Letters Patent is hereby corrected as shown below:

<u>Column 7,</u>
Line 24, insert -- EXAMPLE 2 --.
Line 39, insert -- EXAMPLE 3 --.

<u>Column 8,</u>
Line 36, "2" should read -- 7 --.

Signed and Sealed this

Fifteenth Day of October, 2002

*Attest:*

*Attesting Officer*

JAMES E. ROGAN
*Director of the United States Patent and Trademark Office*